United States Patent [19]

Upsher

[11] Patent Number: 4,517,964
[45] Date of Patent: * May 21, 1985

[54] DUAL BLADED LARYNGOSCOPE

[76] Inventor: Michael S. Upsher, 2957 Adeline Dr., Burlingame, Calif. 94010

[ * ] Notice: The portion of the term of this patent subsequent to Mar. 20, 2001 has been disclaimed.

[21] Appl. No.: 478,850

[22] Filed: Mar. 25, 1983

Related U.S. Application Data

[63] Continuation-in-part of Ser. No. 324,887, Nov. 25, 1981, Pat. No. 4,437,458.

[30] Foreign Application Priority Data

Nov. 27, 1980 [EP] European Pat. Off. ....... 80 107427.9

[51] Int. Cl.³ .............................................. A61B 1/06
[52] U.S. Cl. .................................................... 128/11
[58] Field of Search .................................. 128/10, 11

[56] References Cited

U.S. PATENT DOCUMENTS 2,648,329  8/1953  Morch ................................... 128/11
4,406,280  9/1983  Upsher ................................. 128/11
4,437,458  3/1984  Upsher ................................. 128/11

Primary Examiner—Edward M. Coven
Assistant Examiner—Max F. Hindenburg
Attorney, Agent, or Firm—Flehr, Hohbach, Test, Albritton & Herbert

[57] ABSTRACT

A dual bladed laryngoscope is disclosed herein. This laryngoscope includes a handle configured to operate with a conventional blade carrying its own light source and one which merely carries a light guide. In this regard, the handle also includes a light source along with a power supply and a mounting base, the latter is designed to receive the first-mentioned blade in a way which automatically causes the power supply to energize the light source carried by this blade. At the same time, this mounting base is designed to receive the second-mentioned blade in a way which places its light guide in optical communication with the light source carried by the handle while causing the power supply to energize this latter light source.

14 Claims, 8 Drawing Figures

DUAL BLADED LARYNGOSCOPE

This application is a continuation-in-part of U.S. patent application Ser. No. 324,887, filed Nov. 25, 1981 now U.S. Pat. No. 4,437,458.

The present invention relates generally to laryngoscopes of the type described in applicant's co-pending U.S. application Ser. No. 324,887 filed Nov. 25, 1981 and incorporated herein by reference, and more particularly to a specific dual blade embodiment.

In applicant's co-pending application just recited, a particular laryngoscope handle is illustrated in FIGS. 48, 49 and 50. This handle includes its own light source, a power supply (batteries) and two separate electrical contacts, a first one which projects up from a mounting surface at the top of the handle and a second one which is recessed below the surface. This handle is designed to receive a conventional laryngoscope blade, that is, one carrying its own light source, as well as a blade which only carries a light guide. More specifically, when the conventional light carrying blade is mounted to the handle, it engages the upwardly projecting contact in a way which causes the power supply contained by the handle to energize its light source. Alternatively, when the blade without the light source is mounted to the handle, it engages the recessed contact in a way which causes the power supply to energize the light source carried by the handle. At the same time, the light guide is placed in optical communication with this light source.

While the laryngoscope just described is generally satisfactory for its intended purpose, because its blade body is electrically non-conductive, it does require a specific combination projection/washer arrangement illustrated in FIGS. 51 and 52A for engaging the recessed contact in the handle while, at the same time, engaging the handle body itself, to close the appropriate circuit which energizes the light source carried by the handle.

It is the object of the present invention to provide a laryngoscope embodiment similar to the laryngoscope just described, but one which does not require the projection/washer arrangement illustrated in FIGS. 51 and 52A. Rather, as will be seen hereinafter, in the particular embodiment disclosed herein, the laryngoscope blade which does not include its own light source is constructed entirely of metal (with the exception of its light guide) or at least its mounting base is and it is this mounting base (or the entire blade body) which serves the same purpose as the washer in FIGS. 51 and 52A of the above-recited co-pending application.

The laryngoscope embodiment disclosed herein will be described in more detail hereinafter in conjunction with the drawings wherein.

Figure 4:
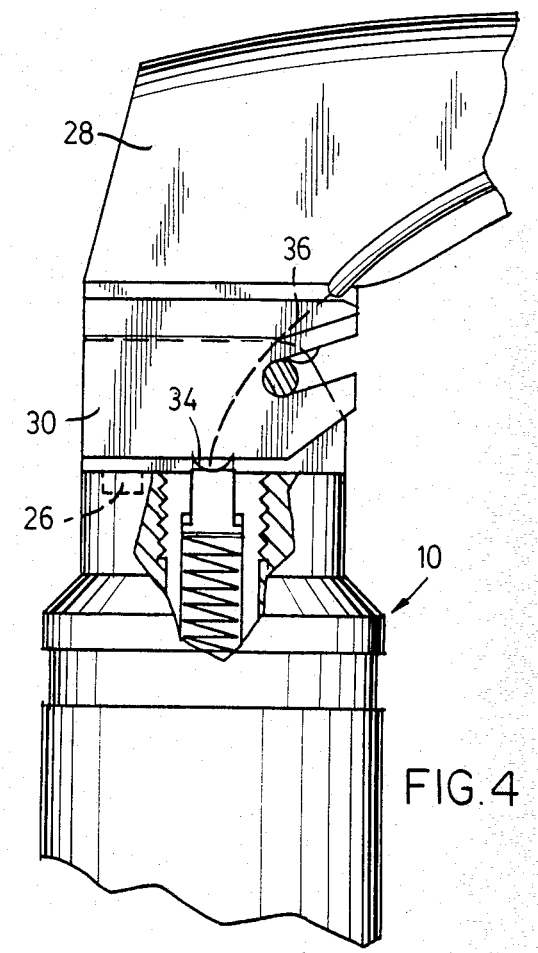
FIG. 4 is a side elevational view of the handle in FIG. 1 in combination with a laryngoscope blade which carries its own light source.
Figure 5:
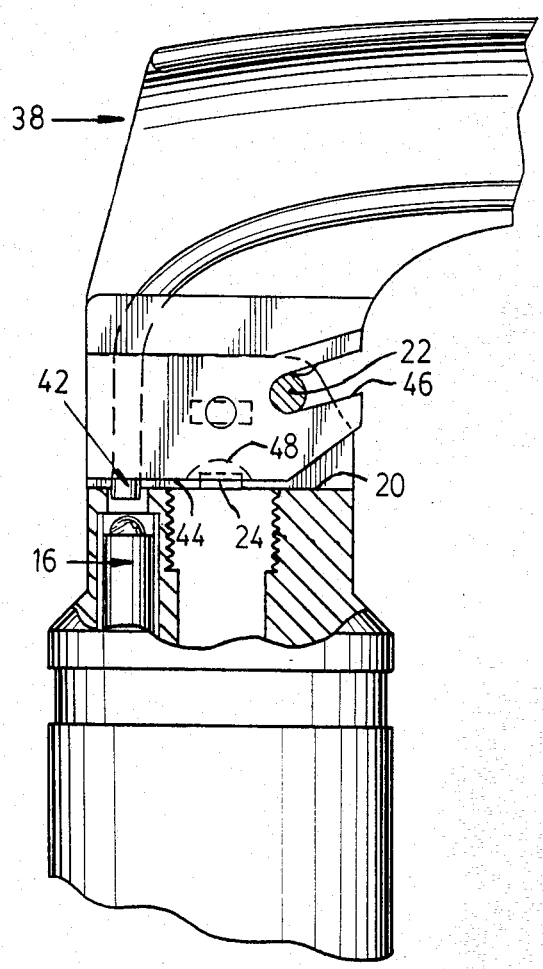
FIG. 5 is also a side elevational view of the laryngoscope handle of FIG. 1 in combination with a different blade, specifically, one which does not include its own light source, but rather a light guide.
Figure 7:
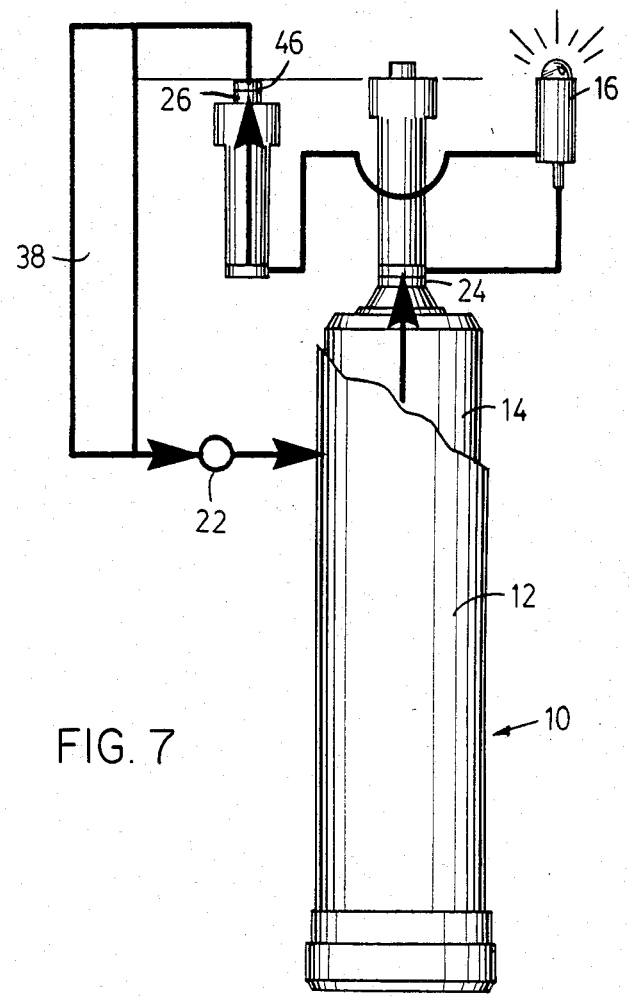
Figure 8:
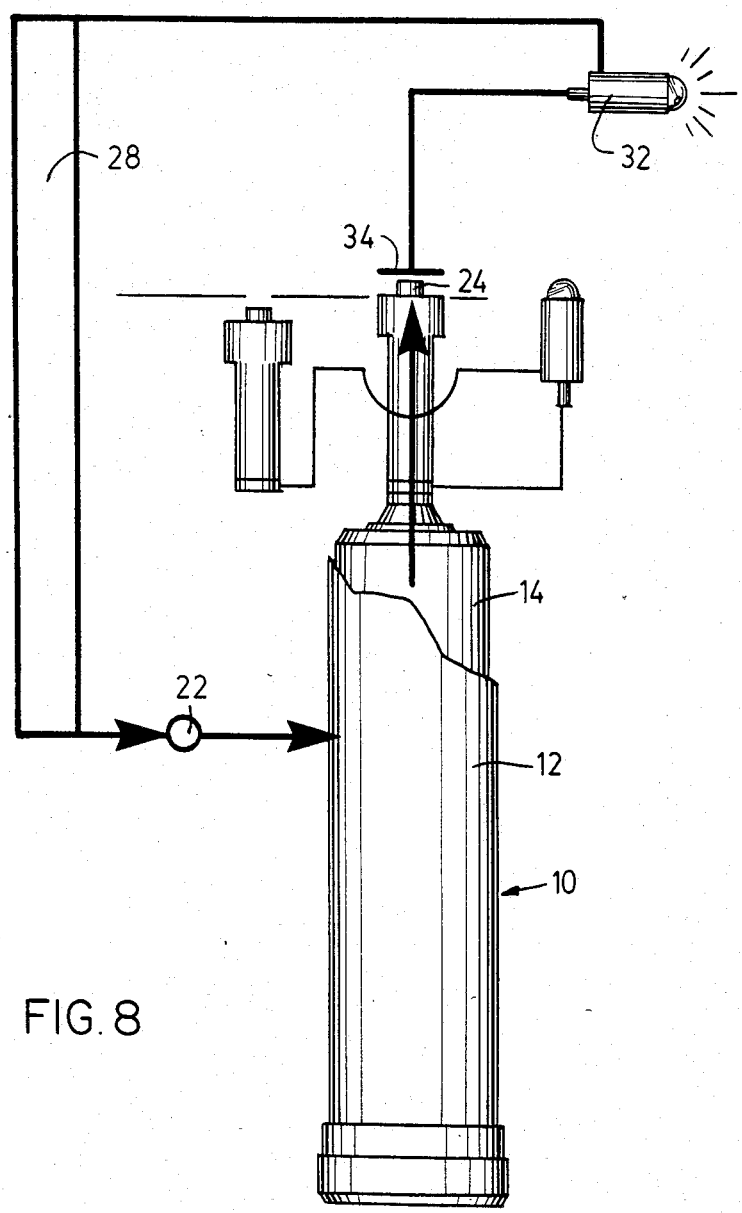

FIGS. 7 and 8 diagrammatically illustrate how the components making up each combination in FIGS. 4 and 5 are electrically connected together.

Figure 2:
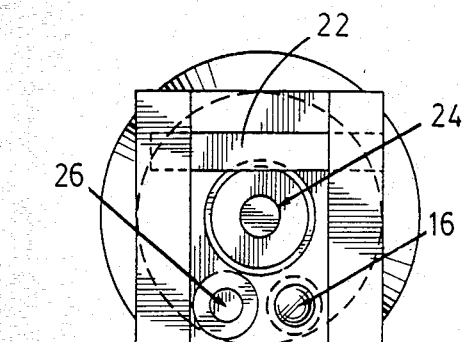
FIG. 2 is a top plan view of the laryngoscope shown in FIG. 1.
Figure 3:
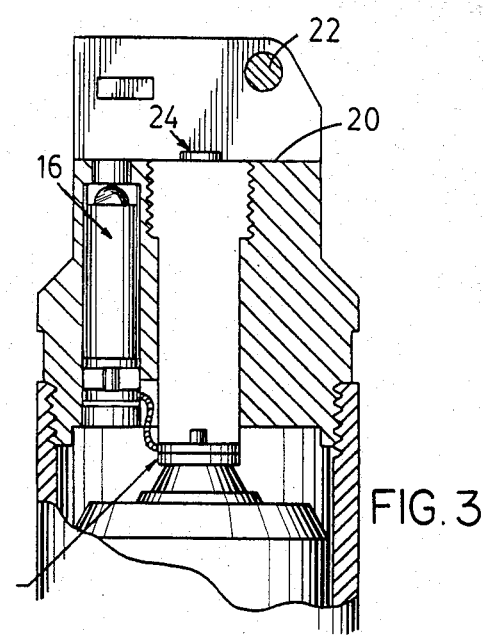
FIG. 3 is a side elevational view of the laryngoscope shown in FIG. 1.
Figure 1:
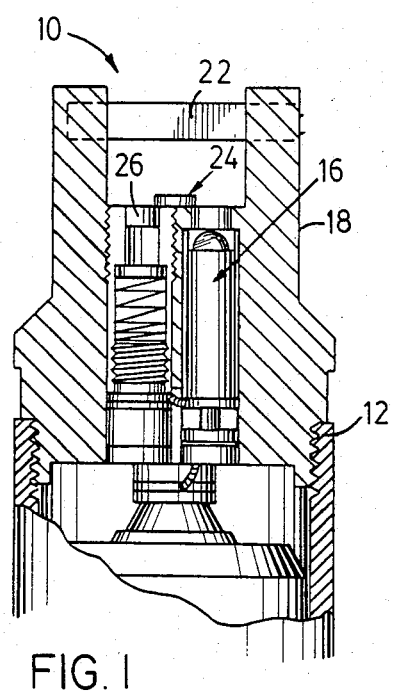
FIG. 1 is a back elevational view of the top end of a laryngoscope handle designed in accordance with the present invention.

Turning now to the drawing, wherein like components are designated by like reference numerals throughout the various figures, attention is directed first to FIGS. 1-3 which show the top end of a laryngoscope handle generally indicated at 10. This handle may be identical to the one illustrated in FIGS. 48 and 49 in applicant's co-pending application Ser. No. 324,887, recited above. As a result, the handle includes an electrically conductive main body 12 containing a suitable power supply 14 (see FIGS. 7 and 8) in the form of one or more batteries. The handle also includes its own light source 16 located at its blade connecting end 18. As seen in FIG. 3, this blade connecting end includes an upwardly facing, relatively flat mounting surface 20 below a mounting bar 22.

In addition to the components thus far described, handle 10 includes two electrical contacts, the first one indicated at 24 which projects up from surface 20 and a second one 26 which is recessed below surface 20. From an electrical circuit standpoint, as seen in FIGS. 7 and 8, electrical contact 24 together with power supply 14 and handle body 12 together form a first open circuit while these same three components along with the light source 16 and the contact 26 form a second open circuit. As will be seen hereinafter, the laryngoscope disclosed herein includes a first blade which closes this first open circuit through its own light source for energizing the latter and a second blade which has no light source but which closes the second circuit for energizing light source 16.

Turning to FIG. 4, laryngoscope handle 10 is shown supporting a conventional laryngoscope blade 28. This blade includes its own mounting base 30, its own light source 32 (see FIG. 8), an electrical contact 34 projecting down from and electrically insulated from base 30, and an electrical lead line 36 electrically connecting the light source to contact 34. The other side of the light source is electrically connected to the blade body which is electrically conductive in its entirety, as best seen in FIG. 8. In this way, when blade 28 is mounted to handle 10, contact 34 engages contact 24. At the same time, the blade body engages the mounting bar 22 of the handle, thereby closing the electric circuit including the laryngoscope handle 12 (through the mounting bar), the power supply 14, contacts 24 and 34, light source 32 and the blade itself, as illustrated in FIG. 4. This automatically causes the power supply to energize the light source 32.

Figure 6:
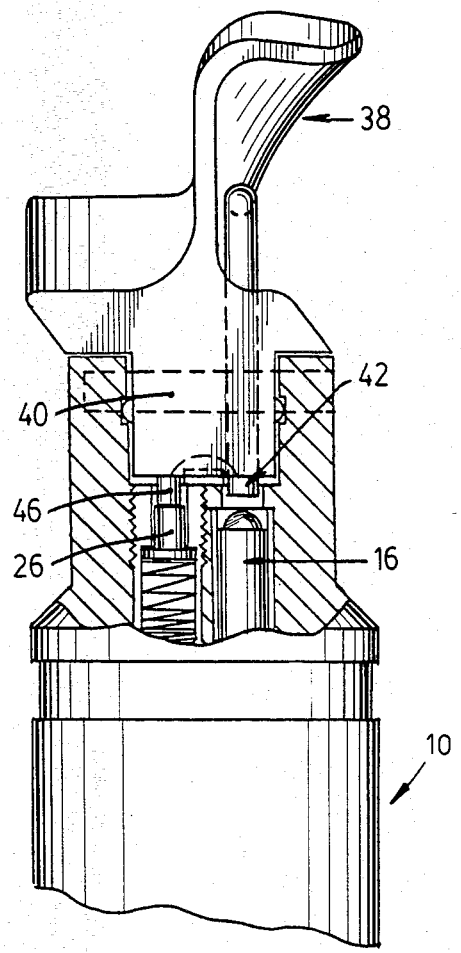
FIG. 6 is a back elevational view of the combination shown in FIG. 5.

Turning to FIGS. 5 and 6, handle 10 is shown supporting a second laryngoscope blade 38 which is also preferably electrically conductive in its entirety or at least its mounting base 40 is electrically conductive. The blade also includes an optical fiber 42 extending from mounting base 40 to the tip of the blade (not shown). In addition, blade 38 includes a relatively flat mounting surface 44 and a channeled jaw 46 such that when the jaw receives mounting bar 22 in the manner illustrated in FIG. 5, surface 44 is placed in confronting relationship with surface 20 at the top of handle 10 (see FIG. 5). At the same time, mounting base 40 includes its own projection 46 extending down from surface 44 and its own opening 48 extending in from the same surface. When blade 38 is mounted to handle 10, projection 46 extends into the opening containing recessed contact 26 for engaging the latter (see FIG. 6). At the same time, opening 48 extends around projecting contact 24 so as to prevent the latter from engaging any part of blade 38.

With blade 38 mounted to handle 10 in the manner just described, contacts 26 and 46 engage one another and the blade body engages the handle body through mounting base 40 and mounting bar 22. Since contact 46 forms an electrically conductive part of the blade (at least its mounting base) contact 46 is placed in electrical engagement with the handle (through mounting bar 22), thereby closing the electrical circuit including the handle 12, power supply 14, light source 16 and the blade itself 38, as illustrated in FIG. 7. This automatically causes the power supply to energize light source 16. At the same time, while not shown, the light guide 42 is placed in optical alignment with light source 16.

The overall dual blade laryngoscope just described differs from the corresponding embodiment in FIGS. 48–52 in applicant's co-pending application Ser. No. 324,887 to the extent that the present embodiment does not require the previously recited washer. Rather, since the entire base 40 of laryngoscope blade 38 is constructed of metal, this base serves to close the circuit between contact 26 and the handle body when blade 38 is mounted in place.

What is claimed is:

1. A laryngoscope comprising: a handle including an electrically conductive handle body, a first light source carried on said body, a power supply means contained within said body, and an uppermost blade connecting end having first and second electrical contacts respectively forming parts of separate first and second open circuits, each including said power supply means and said handle body and said second open circuit including said first light source; a first blade carrying a second light source and means for mounting the first blade to the blade connecting end of said handle in a way which causes said first blade to engage said first contact without engaging said second contact for placing said second light source in circuit with said first open circuit and for closing said first open circuit whereby said power supply means energizes said second light source carried by said first blade while said first light source remains off; and a second blade carrying a light guide and having an electrically conductive base for mounting the second blade with the blade connecting end of said handle in a way which causes said second blade to engage said second contact without engaging said first contact for closing said second open circuit through the electrically conductive mounting base of said second blade whereby said power supply means energizes said first light source carried by said handle while said light guide is placed in optical communication with said first light source.

2. A laryngoscope according to claim 1 wherein said second blade is constructed in its entirety of electrically conducting material, except for said light guide.

3. A laryngoscope according to claim 1 wherein the blade connecting end of said handle includes a first flat surface, wherein said first contact projects up from said surface, wherein said second contact is recessed below said surface and wherein said mounting base of said second blade includes a second flat surface which confronts said first surface when said second blade is mounted to said handle, said mounting base including means projecting out from said second surface for engaging said recessed second contact and a hole in said second surface for preventing the latter from engaging said projecting first contact when said second blade is mounted to said handle.

4. A larynogscope comprising: a handle including an electrically conductive handle body, a first light source carried on said body, a power supply means contained within said body, and an uppermost blade connecting end having a blade connecting mounting bar, a flat mounting surface and first and second electrical contacts respectively forming parts of separate first and second open circuits, each including said power supply means and said handle body including said mounting bar and said second open circuit including said first light source, said first contact projecting out from said mounting surface and said second contact being recessed below said surface; a first blade carrying a second light source and means for mounting the first blade to the blade connecting end of said handle in a way which causes said first blade to engage said first projecting contact without engaging said second recessed contact for placing said second light source in circuit with said first open circuit and for closing said first open circuit whereby said power supply means energizes said second light source carried by said first blade while said first light source remains off; and a second blade carrying a light guide and having an electrically conductive base which includes its own flat mounting surface having a projection extending out from this surface and an opening therein, said base serving to mount said second blade with the blade connecting end of the handle in a way which causes the projection carried by said base to engage said second contact while the opening in said base prevents the blade from engaging said first contact for closing said second open circuit through the mounting base of said second blade, whereby said power supply means energizes said first light source carried by said handle while said light guide is placed in optical communication with said first light source.

5. A laryngoscope blade for use in a laryngoscope including a handle having battery means, a light source, first electrical contact means for electrically connecting said battery means to said light source for energizing the latter when said blade is disengagably connected with said handle in predetermined contacting relationship with said first contact means, and second electrical contact means for electrically connecting said battery means to a second light source on a second laryngoscope blade for energizing said second light source when the second blade is disengagably connected with the handle in predetermined contacting relationship with said second contact means, said first-mentioned laryngoscope blade comprising:

a blade body carrying a light guide and having a base section including means for disengagably connecting said blade body to said handle in contacting relationship with said first contact means for energizing said first light source while at the same time placing one end of said light guide in optical alignment with said first-mentioned light source, said base being configured so as not to contact said second contact means.

6. A blade according to claim 5 wherein said second contact means projects out from a specific surface of said handle and wherein the base of said blade body includes a surface having an opening sufficiently large to receive said second contact means without the latter touching the blade when the blade is disengagably connected to said handle.

7. A blade according to claim 5 wherein said first contact means is recessed within an opening in a specific surface of said handle and wherein the base of said blade body includes projecting means configured to enter said opening and contact said first contact means when said blade is disengagably connected to said handle.

8. A blade according to claim 7 wherein said second contact means projects out from a specific surface of said handle and wherein the base of said blade body includes a surface having an opening sufficiently large to receive said second contact means without the blade touching said second contact means when the blade is disengagably connected to said handle.

9. A blade according to claim 5 wherein said base section is electrically conductive.

10. A laryngoscope blade for use in a laryngoscope including a handle having battery means, a light source, and electrical contact means recessed within an opening in a specific surface of said handle for energizing said light source when said blade is disengagably connected with said handle in a predetermined contacting relationship with said contact means, said laryngoscope blade comprising:

a blade body carrying a light guide and having an electrically conductive base section including means for disengagably connecting said body to said handle while placing one end of said light guide in optical alignment with said light source, said base section also including projecting means configured to enter said opening and engage said contact means when said blade is disengagably connected to said handle for electrically connecting said battery means to said light source in order to energize the latter.

11. A blade according to claim 10 wherein said handle includes second electrical contact means projecting up from said specific surface of said handle for electrically connecting said battery means to a different light source on a second laryngoscope blade for energizing said different light source when said second blade is disengagably connected with the handle in a predetermined contacting relationship with said second contact means and wherein the blade body of said first-mentioned blade includes a surface having an opening specifically positioned and sufficiently large to receive said second contact means without the latter touching said blade when said blade is disengagably connected to said handle.

12. A laryngoscope blade comprising: a blade body having a forwardmost end and a rearwardmost end, the latter defining a mounting base having means for mounting the blade to a cooperating laryngoscope handle such that a specific surface of said base is in confronting relationship with a cooperating surface of said handle; a light guide carried by said blade and extending from its rearwardmost end at said base to its forwardmost end at the forwardmost end of said blade body such that the rearwardmost end of the light guide is placed in optical alignment with a light source carried by said handle when the base of said blade is mounted to said handle; and electrical contact means projecting from said specific surface of said base, said contact means being adapted to engage a cooperating contact means on said handle for causing said light source to energize when the base of said blade is disengagably connected to said handle.

13. A blade according to claim 12 wherein said mounting base is electrically conductive.

14. A laryngoscope blade according to claim 12 wherein said specific surface of the base of said blade body includes an opening configured to receive a second, projecting contact means forming part of said handle such that the second contact means does not engage the blade when the base of the blade is disengagably connected to the handle.

* * * * *